(12) United States Patent
Pfister et al.

(10) Patent No.: US 7,495,233 B2
(45) Date of Patent: Feb. 24, 2009

(54) FLUORESCENCE SCANNER FOR MOLECULAR SIGNATURES

(75) Inventors: Marcus Pfister, Erlangen (DE); Wolfgang Strob, Erlangen (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 11/375,948

(22) Filed: Mar. 15, 2006

(65) Prior Publication Data

US 2006/0249690 A1     Nov. 9, 2006

(30) Foreign Application Priority Data

Mar. 18, 2005   (DE)   ........................ 10 2005 013 045

(51) Int. Cl.
 *H05B 35/00*   (2006.01)
(52) U.S. Cl. .................................................. 250/458.1
(58) Field of Classification Search ............. 250/484.2, 250/484.3, 458.1; 600/160
See application file for complete search history.

(56) References Cited

U.S. PATENT DOCUMENTS

| | | | |
|---|---|---|---|
| 4,951,133 A | 8/1990 | Onoda | |
| 6,191,406 B1 * | 2/2001 | Nelson et al. | 250/208.1 |
| 6,377,700 B1 | 4/2002 | Mack et al. | |
| 6,443,960 B1 | 9/2002 | Brabrand et al. | |
| 6,471,636 B1 | 10/2002 | Sano et al. | |
| 6,669,093 B1 * | 12/2003 | Meyerson et al. | 235/472.01 |
| 7,119,351 B2 * | 10/2006 | Woelki | 250/559.4 |
| 2001/0009269 A1 * | 7/2001 | Hayashi | 250/458.1 |
| 2002/0138008 A1 | 9/2002 | Tsujita et al. | |
| 2002/0162976 A1 * | 11/2002 | Birk et al. | 250/548 |
| 2003/0139661 A1 | 7/2003 | Kimch et al. | |
| 2003/0191368 A1 | 10/2003 | Wang et al. | |
| 2004/0028188 A1 * | 2/2004 | Amann et al. | 378/209 |

(Continued)

FOREIGN PATENT DOCUMENTS

DE     44 12 164 A1     10/1995

(Continued)

OTHER PUBLICATIONS

German Office Action dated Aug. 3, 2006 and translation.

(Continued)

*Primary Examiner*—David P Porta
*Assistant Examiner*—Marcus H Taningco
(74) *Attorney, Agent, or Firm*—Brinks Hofer Gilson & Lione

(57) ABSTRACT

An apparatus detects fluorescence. The apparatus, also known as a fluorescence scanner, includes an image detector, which is embodied for detecting image data in the wavelength range of fluorescent light, and an excitation light source, which is embodied for generating light in a wavelength range suitable for exciting the fluorescence. The apparatus has a guide beam projector, which is embodied for generating a guide beam from light in the visible wavelength range. The guide beam is aimed such that a projection of the guide beam, a region that is detectable by the image detector is displayed. The guide beam allows exact viewing of a body region to be examined possible for the surgeon, which is not possible on the basis only of the light for exciting a fluorescence, at least whenever the excitation light is in the non-visible wavelength range, such as IR or NIR, or is generated directly during the recording of the fluorescence image.

11 Claims, 3 Drawing Sheets

U.S. PATENT DOCUMENTS

| | | | |
|---|---|---|---|
| 2004/0031931 | A1 | 2/2004 | Mueller et al. |
| 2004/0037454 | A1 | 2/2004 | Ozawa et al. |
| 2004/0169854 | A1 | 9/2004 | Vo-Dinh et al. |
| 2004/0217260 | A1* | 11/2004 | Bernardini et al. ....... 250/208.1 |
| 2004/0249245 | A1 | 12/2004 | Irion |
| 2005/0027166 | A1 | 2/2005 | Matsumoto et al. |
| 2005/0068534 | A1 | 3/2005 | Kleinfeld et al. |
| 2005/0073729 | A1 | 4/2005 | Schmid et al. |
| 2005/0148842 | A1 | 7/2005 | Wang et al. |

FOREIGN PATENT DOCUMENTS

| | | |
|---|---|---|
| DE | 1999 83 341 T1 | 1/2000 |
| DE | 195 35 114 A1 | 10/2002 |
| EP | 1 374 755 A1 | 1/2004 |
| WO | WO 97/33157 | 9/1997 |
| WO | WO 02/41794 A1 | 5/2002 |
| WO | WO 03/077749 A2 | 9/2003 |
| WO | WO 03/105485 B1 | 12/2003 |

OTHER PUBLICATIONS

Novadaq Technologies Inc.: "SPY Intra-operative Imaging System", 2 pages; printed on Feb. 7, 2006 and located at http://www.novadaq.com/spy_imaging_system.php.

U. Mahmood et al., Near-Infrared Optical Imaging of Protease Activity for Tumor Detection; Radiology vol. 213, No. 3; pp. 866-870 and Dec. 1999.

A. Hengerer et al. "Molecular Biology for Medical Imaging," Electromedia vol. 69, No. 1; pp. 44-49; 2001.

http://www.ehendrick.org/healthy/001004.htm; printed on Feb. 7, 2006; 2 pages.

"New Multichannel Fluorescence Reflectance Imaging System for Small Animal Applications," by A. Wall et al.; European radiology, 2003, Supplement to vol. 13, p. 303.

"Multispectral Fluorescence Imager May Guide Surgical Procedure," by B.D. Butkus; Biophotonics, vol. 10, No. 4; pp. 18-19; May 2003.

Cri Products: In-Vivo Imaging, & Fluorescence Microscopy website pages; located at http://www.cri-inc.com/products/index.asp; 10 pages and printed on Dec. 22, 2005.

"Imaging Enzyme Activity and Gene expression in Vivo Through a 2.7F Catheter Feasibility Study in Mice," by M. Funovics et al.; Radiology vol. 231, No. 3; pp. 659-666 and Jun. 2004.

Xillix—Seeing Cancer in a New Light; Xillix Technologies Corp.; located at http://www.xillix.com/index_home.cfm; printed on Feb. 7, 2006 and 1 page.

* cited by examiner

FLUORESCENCE SCANNER FOR MOLECULAR SIGNATURES

BACKGROUND

The present embodiments relate to devices for detecting fluorescence.

Equipment for fluorescence detection, hereinafter also called fluorescence scanners, can be used to detect various molecular factors. Substances having different molecular properties may have different fluorescent properties, which can be detected in a targeted way. Fluorescence detection is optically based and is noninvasive or minimally invasive. With the knowledge of the applicable fluorescent properties, the molecular nature of a given material being examined may be ascertained.

In medicine, molecular properties, for instance also called a "molecular signature", provide information about the state of health of a living creature or patient and can be assessed diagnostically. For example, molecular signatures are used for detecting cancer. Still other syndromes, such as rheumatoid arthritis or arteriosclerosis of the carotid artery, can be identified.

For fluorescence detection, the fluorescence is excited, such as by optical excitation. The excitation light is in the infrared range (IR), for instance, or in the near infrared range (NIR). The suitable frequency range is dependent on the substance to be examined. Substances that themselves have no molecular or chemical properties that would be suitable for fluorescence detection can be molecularly "marked" in a suitable way. For instance, markers that with suitable preparation bind to or are deposited only on very special molecules may be used. Such marking may function by a mechanism that in pictorial terms can be thought of as a lock-and-key mechanism. The marker and the molecule to be detected fit one another like a lock and key, while the marker does not bind to other substances. If the marker has known fluorescent properties, then after the binding or deposition, the marker may be optically detected. The detection of the marker allows conclusions to be drawn as to the presence of the marked special substance. For detection, a detector is capable of detecting light in the wavelength that the substance in question, or precisely the marker used, emits upon excitation.

Fluorescence methods examine regions near the surface or in the open body (intraoperative applications). Examples of such investigations are detecting fluorescently marked skin cancer or the detection of tumor boundaries in the resection of fluorescently marked tumors. For example, the company known as NOVADAQ has developed a system for intraoperatively viewing coronary arteries and the function of bypasses (that is, the flow through them).

One subject of research in biotechnology is fluorescent metabolic markers that accumulate only in certain regions, such as tumors, infections, or other foci of disease, or are distributed throughout the body but are activated only in certain regions, for instance by tumor-specific enzyme activities with additional exposure to light.

In medical diagnosis, marker substances, so-called fluorophores, such as indocyanin green (ICG), are known. The marker substances, for example, bind to blood vessels and can be detected optically. In an imaging process, the contrast with which blood vessels are displayed may be enhanced. So-called "smart contrast agents" may be used. These are activatable fluorescence markers that bind, for instance, to tumor tissue and whose fluorescent properties are not activated until the binding to the substance to be marked occurs. Such substances may comprise self-quenched dyes, such as Cy5.5, which are bound to larger molecules by way of specific peptides. The peptides can in turn be detected by specific proteases, produced for instance in tumors, and can be cleaved. The fluorophores are released by the cleavage and are no longer self-quenched, but instead develop fluorescent properties. The released fluorophores can be activated for instance in the near IR wavelength range of around 740 nm. One example of a marker on this basis is AF 750 (Alexa Fluor 750), with a defined absorption and emission spectrum in the wavelength range of 750 nm (excitation) and 780 nm (emission).

In medical diagnosis, such activatable markers may be used, for instance, for intraoperative detection of tumor tissue. The diseased tissue may be identified exactly and then removed. One typical application is the surgical treatment of ovarian cancer. The diseased tissue is typically removed surgically. Because of the increased sensitivity of fluorescence detection, the diseased tissue can be better detected along with various surrounding foci of disease and thus removed more completely.

In the treatment of breast cancer, typical surgical treatments are lumpectomies (or mastectomies) and lymph node sections and lymph node biopsies. Lymph nodes are typically detected optically by means of 99mTc sulfur colloids in combination with low-molecular methylene blue. The radioactive mTc sulfur colloids could be avoided by using fluorescence detection.

In treating these diseases named as examples as well as other syndromes, an operation is typically performed to surgically remove diseased tissue. For aiding in the operation, a fluorescence detection may be performed to improve the detection of the diseased tissue portions to be removed during the ongoing operation or in the open wound. To that end, the tissue parts are marked before the operation with a suitable substance that is then activated by binding to the diseased tissue parts. An apparatus for fluorescence detection should be easy for the surgeon to manipulate and should be usable in the sterile field of the operating room.

BRIEF SUMMARY

The detection of a region marked fluorescently is done by exposing the region to light in the special excitation wavelength of the fluorescent dye, and detecting the emitted light in the corresponding emission wavelength of the fluorophore. A fluorescence scan is made by recording a fluorescence image on the basis of fluorescent light along with an optical image based on visible light. The optical image and the fluorescence image are superimposed to display the fluorescence in the context of the visual image. The fused image with the fluorescently marked tissue is displayed on a small screen on the fluorescence scanner or on an external computer with image processing software. From the superimposed view of the optical and fluorescence images on a display device, the surgeon may detect the tumor tissue and locate the tumor tissue in the body of the patient.

Typically, the excitation of the fluorescence of the marker is done by light, and the detection device has a light source of adequate intensity in order to penetrate the tissue to be examined down to a depth of from 0.5 to 1 cm. In addition, an optical detector is capable of detecting the fluorescent light and, if the fluorescent light is not in the visible wavelength range, to record an image in the visible wavelength range.

The fluorescent light is often in the infrared wavelength range (IR) or the near infrared wavelength range (NIR). Excitation light of a suitable wavelength, which for fluorescence, is typically in the near IR range up to 700 nm. Adequate intensity for sufficient penetration of tissue may be attained with the known illuminants only with relatively low efficiency. Given adequate intensity in the wavelength range of interest, the heat production may be large because of the low efficiency. Simultaneously, the energy consumption for generating the excitation light is considerable. A power-cord energy supply for furnishing the required energy may make the device inconvenient to manipulate, however, and precisely in the operating room area, where work must be done in a restricted space, may be a great hindrance. Moreover, in the sterile field, active cooling of the illuminants, for instance by fans, cannot be done since adequate sterilization of an actively cooled device is undesired.

If a scan based on fluorescence is generated by light in the IR or NIR range, then the surgeon cannot see the excitation light. If fluorescence scanners that do not generate the excitation light continuously, for instance for the sake of saving energy, or that generate it only at the moment the scan is generated, are used, then this problem similarly exists. In these cases, it is not readily possible for the surgeon to aim the scanner exactly at the tissue to be examined. Under some circumstances, this may cost the surgeon valuable time, since the surgeon might have to make several blind tests until the scanning region is viewed as desired.

The fluorescence scanner may generate optical images on an ongoing basis so that the surgeon can observe the images in real time. The optical images correspond to an image detail within which the scanner records fluorescence images. The surgeon can aim the scanner on the basis of the optical images. Once aimed, the fluorescence scanner is activated. The continuous operation of the optical image detector, such as a CCD camera, may substantially increase energy consumption. The surgeon, while aiming the scanner, may have to direct his attention at the screen display of the optical images, instead of being able to keep looking at the patient or body to be examined.

A fluorescence scanner may permit both aiming and viewing without having to do so at the cost of substantially increased energy consumption, and without the user having to take his attention away from the body to be examined.

An apparatus for detecting fluorescence, hereinafter also called a fluorescence scanner, includes an image detector, which is embodied for detecting image data in the wavelength range of fluorescent light, and an excitation light source, which is embodied for generating light in a wavelength range suitable for exciting the fluorescence. The apparatus has a guide beam projector, which is embodied for generating a guide beam from light in the visible wavelength range. The guide beam is aimed such that on the basis of a projection of the guide beam, a region detectable by the image detector is displayed. The image detector can be embodied for instance as a CCD chip, but other imaging technologies can be employed.

A guide beam of this kind, also called an alignment beam, saves the surgeon time. The surgeon may purposefully take pictures of the body region to be examined without having to make several time-consuming blind attempts to view the body region. In addition, using a guide beam may reduce both energy consumption and the heat development in the fluorescence scanner. A portable, battery-operated fluorescence scanner may be provided. The portable fluorescence scanner may operate work in an energy-saving way and be sterilizable for use in the area of the operating room.

A tripping device, such as a button, is provided. By actuating the tripping device, the recording of a fluorescence image is tripped. The guide beam is switched off by the actuation of the tripping device to assure that the light of the guide beam does not wash out the fluorescent light and thus discolor or ruin the fluorescence image.

The guide beam is generated by at least one laser diode in one embodiment. A laser diode generates light that is perceptible, as in the case of a laser pointer, for instance. The laser diode may also operate in an energy-saving way, which is especially advantageous in the case of portable, battery-operated versions of the fluorescence scanner.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND THE PRESENTLY PREFERRED EMBODIMENTS

Figure 1:
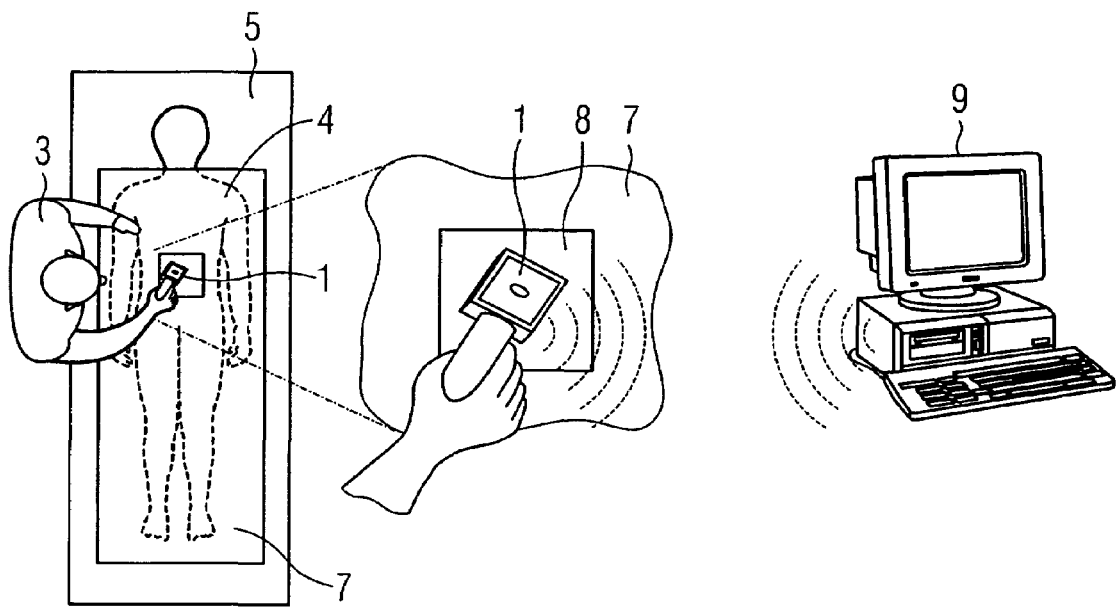
FIG. 1 is an exemplary application scenario for a fluorescence scanner.

FIG. 1 schematically illustrates a scenario for using a fluorescence scanner 1 in one embodiment. A body 4 to be examined, covered by an OR drape 7, lies on an operating table 5. A surgeon 3 treats a region of the body 4 through an opening in the OR drape 7. The surgeon 3 holds a fluorescence scanner 1 in his hand, and, with the fluorescence scanner 1 examines the body region to be treated.

The region 8 of the body 4 to be examined is shown schematically and enlarged. The body 4 is covered by the OR drape 7, except for an opening in the OR drape 7. The surgeon 3 aims the fluorescence scanner 1 centrally at the body region 8, which can be seen and reached through the opening.

Data detected by the fluorescence scanner 1 is transmitted in cordless fashion, as graphically represented in the drawing, to a PC workstation 9. Wired transmission may be used. The PC workstation 9 displays the data received as image data of the body region 8 to be examined on a screen. The surgeon 3 can view the fluorescence scan on the screen of the PC workstation 9, providing the outcome of the scan immediately in front of his eyes. The surgical strategy or planning is oriented to the fluorescence scan as needed.

To enable orientation to the image shown, the optical view of the fluorescence scan has a view of the same visible region or the same body region 8 superimposed on it, in the form of a normal image in the visible wavelength range. On the basis of the image in the visible wavelength range, the physician may recognize details of the body region 8 on the screen. From the superimposed fluorescence scan, the surgeon may associate the outcome of the scan with the actually visible points in the body region 8. Superimposition of an image made in the visible wavelength range may more likely be used where the fluorescence is in a nonvisible wavelength range, such as IR. Non-superposed imaging may be used, such as displaying the images adjacent to each other or sequentially.

Figure 2:
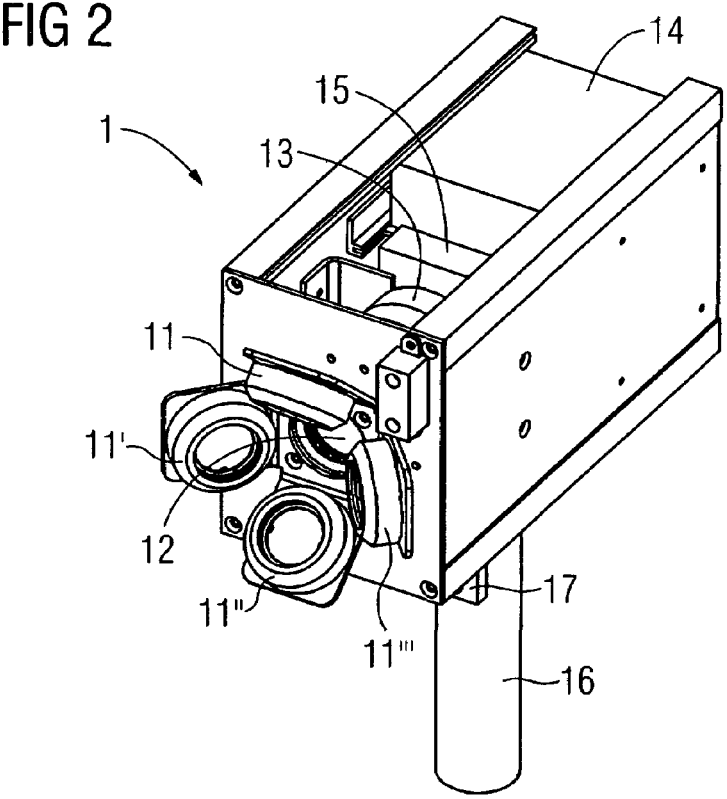
FIG. 2 is a perspective view of a fluorescence scanner of one embodiment with its housing open.

In FIG. 2, a fluorescence scanner 1 is shown in perspective view. The upper covering of the housing is left out for ease of description herein. The fluorescence scanner 1 has a handle 16 for manipulation by the surgeon. On the handle 16, there is a button 17, with which the physician may manually trip a fluorescence scan.

In the front region, excitation light sources 11, 11', 11'', 11''' are arranged to illuminate a region at a distance of approximately 6 to 10 cm. The light sources 11, 11', 11'', 11''' are arranged at an angle of approximately 45° to the front panel. This arrangement may provide an optimal working distance since the scanning region should not be touched and too great a distance would require excessively high excitation light intensity. Other distances and/or angles may be used.

The excitation light sources 11, 11', 11'', 11''' may be halogen illuminants, but may be LEDs (light emitting diodes). Since an individual LED has a relatively low luminous intensity, LED arrays on the order of magnitude of 60 LEDs each are used for each light source. Each of the total of four LED arrays have a total luminous power of approximately 0.25 to 1 Watt.

A lens 12 on the fluorescent scanner 1 is aimed frontally at the illuminated region. Fluorescent light, normal light and ambient light may reach the fluorescence scanner 1 through the lens 12. So that the fluorescent light will not be washed out by the ambient light, a filter essentially allows fluorescent light, but not light in the visible wavelength ranges, to pass through. To enable making an optical image in the visible wavelength range, a filter changer, not shown in detail in the drawing, can for instance change to a filter that allows light in the visible wavelength range to pass through. Depending on the optical properties of the entire construction, the filter may be dispensed with for taking the optical image, and the filter changer remove the filter from the beam path. To that end, a fold-down mechanism may for instance be used, of the kind known from single lens reflex cameras.

Light that has passed through the lens 12 and the filter reaches a CCD camera 15. The CCD camera 15 is capable of recording images both in the wavelength range of visible light and in the wavelength range of the fluorescence. The image data recorded by the CCD camera 15 is received by a data acquisition unit 14 and transmitted to the outside, preferably in cordless fashion.

One exemplary embodiment of a mode of operation provides that the fluorescence scanner 1 is initially operated in standard fashion, such that normal images are made in the visible wavelength range. In the filter changer 13 either no filter or a filter that allows visible light to pass through is located in the beam path. As soon as the surgeon 3 has viewed the body region 8 in question, the surgeon trips a fluorescence scan. The tripping causes the image in the visible wavelength range to be stored in memory.

A suitable filter is inserted that substantially allows only light in the fluorescent wavelength range to pass through. The excitation light sources 11, 11', 11'', 11''' are activated. A fluorescence scan is stored in memory. From this sequence, if performed fast enough, the storage in memory of one optical and one fluorescence image can be achieved from virtually the same viewing angle and can then be superimposed on one another.

Figure 3:
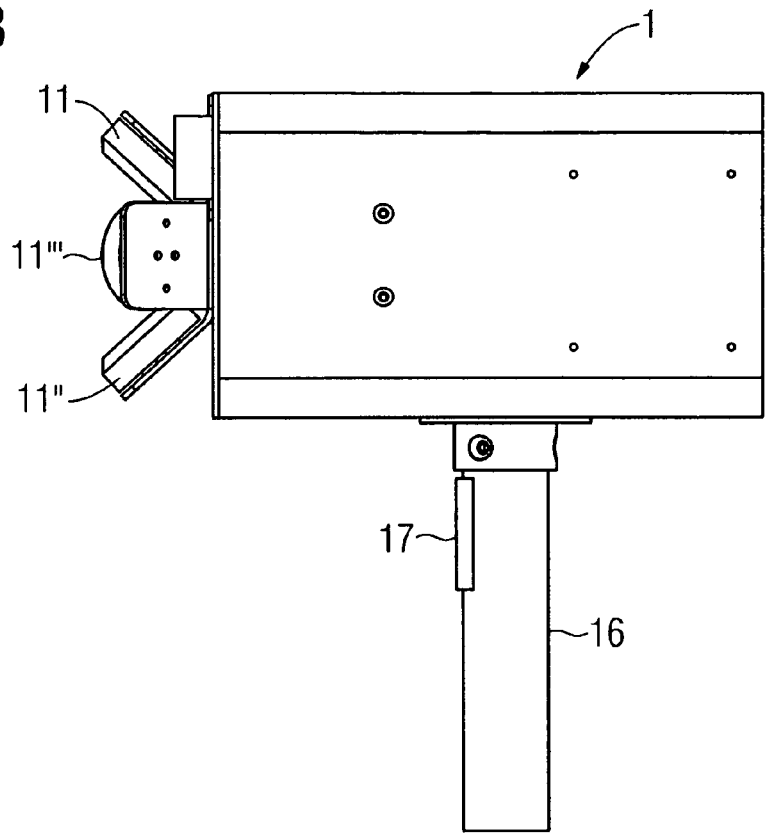
FIG. 3 is a side view of a fluorescence scanner of FIG. 2.

In FIG. 3, the fluorescence scanner 1 is shown in a side view. The handle 16 with the button 17 is shown, as are the excitation light sources 11, 11', 11'', located on the front of the housing. The side view makes the angle of approximately 45° visible that the excitation light sources 11, 11' form with the housing.

Figure 4:
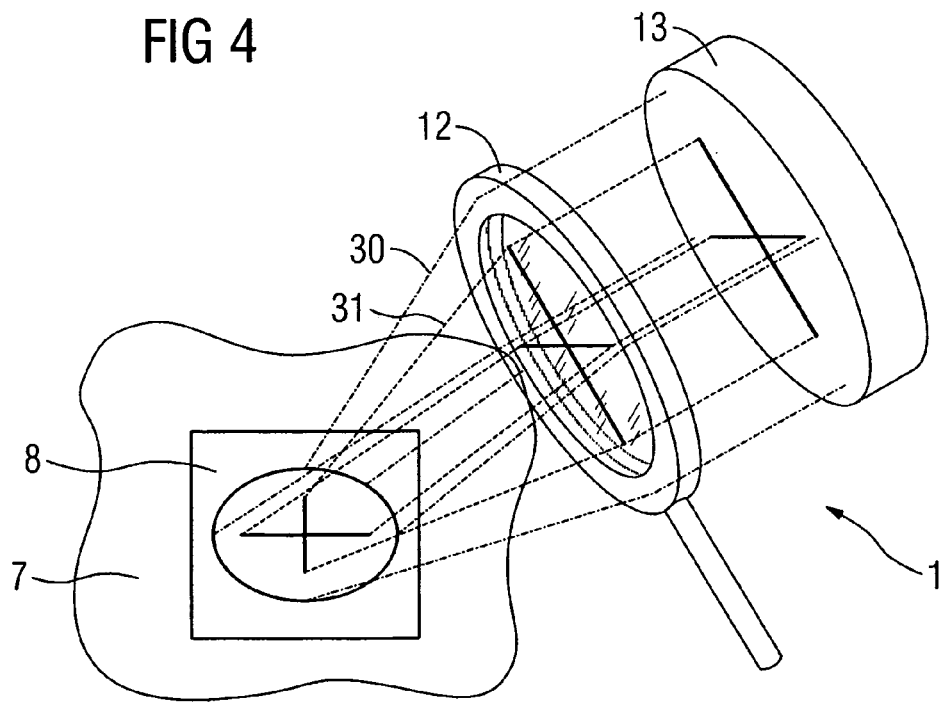
FIG. 4 is a schematic view of one embodiment of a guide beam.

In FIG. 4, the guide beam 30 is shown schematically. The guide beam 30 is projected onto the scanning region 8 of the body to be examined, which is accessible through the opening in the surgical drape 7.

The guide beam projector 13 inside the fluorescence scanner 1, the latter not further shown in the drawing, generates a guide beam 30 in the form of crosshairs. To that end, the guide beam projector 13 includes illuminants which are capable of generating two fans of light that are perpendicular to one another. The two perpendicular fans of light pass through the lens 12 of the fluorescence scanner 1 and are projected onto the scanning region 8. On the scanning region, the two fans of light are reproduced in a form of a crosshair-like light cross 31. Other guide beam shapes may be used.

The light cross 31 is aimed such that it is located centrally in the region to be scanned by the fluorescence scanner 1. In other words, the light cross 31 is projected into the center of the region of which a fluorescence image is being or to be taken.

To enable the surgeon to perceive the light cross 31, the light cross 31 is formed by light in the visible wavelength range. For generating visible light, LEDs are use as illuminants in one example. Other illuminants may be used, such as laser diodes, of the kind used in a laser pointer, for instance. Still other illuminants, such a halogen lamps or incandescent bulbs, may be provided.

During the operation of the fluorescence scanner 1, the light cross 31 is switched off in order not to adulterate or wash out the fluorescence image. This can easily be coupled with the tripping device for tripping the scan. For example, the light cross 31 is switched off by actuation of the tripping device, such as the above-described button 17 of the fluorescence scanner 1. Using the light cross, the surgeon can aim the fluorescence scanner 1. The light cross 31 is not deactivated until the aiming has been concluded.

The light cross 31 need not necessarily be switched off, however, since for taking the fluorescence image a filter is used anyway that filters out light in the visible wavelength range, which would wash out the fluorescence image. Conversely, the guide beam 30 is not switched on automatically and can be switched on manually by actuation of a tripping device, such as a further button.

Figure 5:
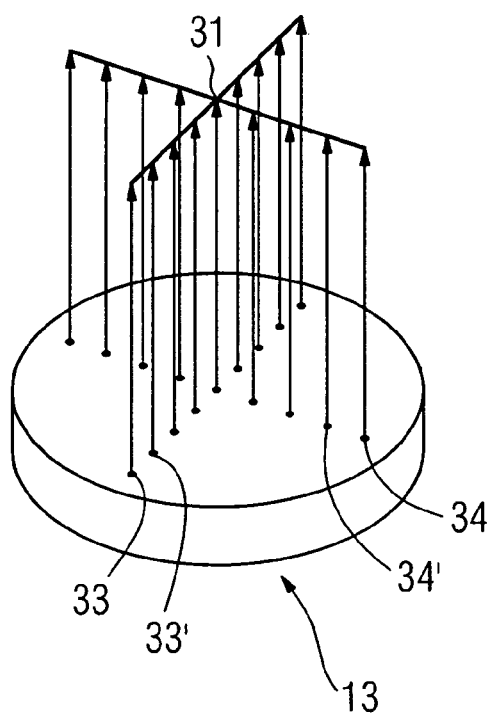
FIG. 5 shows illuminants in the guide beam projector in one version.

FIG. 5 shows an array of illuminants 33, 33', 34, 34' on the guide beam projector 13 for generating the light cross 31. The illuminants 33, 33', 34, 34' are arranged such that a first group of illuminants 33, 33' projects a light fan in a first plane. A second group of illuminants 34, 34' projects a light fan in a second plane. The respective projection planes are indicated by lines in the drawing.

The light fans that are perpendicular to one another, on being projected onto a plane or onto the scanning region 8 to be examined, form a light cross 31. The generation of the light cross 31 by two light fan planes may not be dependent on the distance from the scanning region. The light cross 31 is generated independently of the distance, since the array of illuminants 33, 33', 34, 34' has no parallax in this respect.

Figure 6:
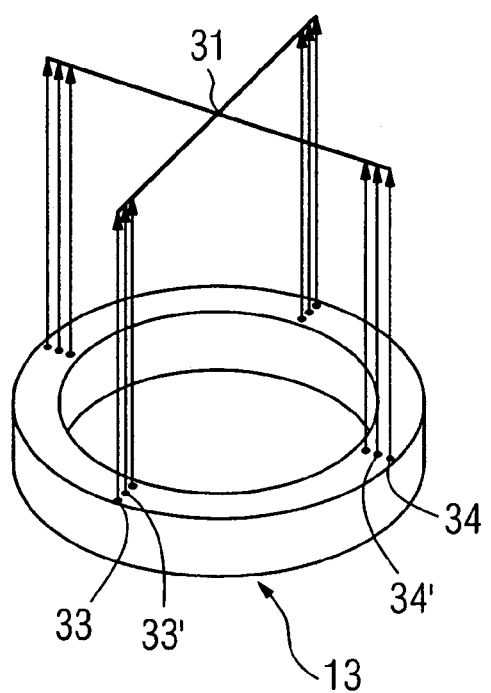
FIG. 6 shows illuminants in the guide beam projector in another version.

FIG. 6 shows schematically a further array of illuminants 33, 33', 34, 34' making it possible to generate a light cross 31 without parallax. The array of illuminants 33, 33' on the one hand and the illuminants 34, 34' on the other that is shown also makes it possible to generate two light fans perpendicular to one another.

However, the illuminants 33, 33', 34, 34' are not located in the center of the guide beam projector 13 but instead only on its periphery. This arrangement makes it possible in particular for light from the scanning region 8 to pass through the guide beam projector 13 on its way to the CCD camera 15. In this arrangement, the guide beam projector 13 may either be embodied only annularly, or, in the annular array, an optical filter may be provided such as the filter required for fluorescence images for filtering out light in the visible wavelength range.

In a further version, not shown, the guide beam projector 13 generates a single beam of light, in the manner of a laser pointer, that projects a point like light spot or other pattern. In order to remain independent of the distance from the scanning region 8, the beam of light should be located centrally in the optical connection between the scanning region 8 and the CCD camera 15. With a central location, parallax problems are avoided, and the light spot is always projected into the center of the scanning region 8, regardless of the distance. Non-parallax arrangements may be used.

The central location of the beam of light can be attained on the one hand by a central location of the applicable illuminant. A disadvantage of such an arrangement, however, is that the illuminant is a hindrance to taking both optical images and fluorescence images and causes a kind of "blind spot". On the other, to avoid this problem, the illuminant may instead be located noncentrally, or in other words outside the optical path between the scanning region 8 and the CCD camera 15. The beam of light of the illuminant can be incorporated into the optical path by a one-way mirror. The one-way mirror is located in the optical path and has the function of being passable to light that is capable of reaching the CCD camera 15 but of reflecting light from the illuminant in such a way that it is incorporated centrally into the optical path.

In a further version, also not shown, the guide beam projector 13 generates a rectangular projection, which outlines the scanning region 8 detectable by the CCD camera 15. Other forms of the guide beam 30 can readily be imagined.

The embodiments relate to an apparatus 1 for detecting fluorescence. The apparatus, also known as a fluorescence scanner, includes an image detector which is embodied for detecting image data in the wavelength range of fluorescent light and an excitation light source 11, 11', 11", 11''' which is embodied for generating light in a wavelength range suitable for exciting the fluorescence. The apparatus has a guide beam projector 13 for generating a guide beam 30 from light in the visible wavelength range. The guide beam 30 is aimed such that on the basis of a projection of the guide beam 30, a region that is detectable by the image detector is displayed. This kind of visible guide beam 30 allows exact viewing of a body region to be examined possible for the surgeon.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. An apparatus for detecting fluorescence, the apparatus comprising:
    an image detector operable to detect image data of a region in a wavelength range of fluorescent light;
    an excitation light source operable to generate light in a wavelength range suitable for exciting the fluorescence; and
    a guide beam projector operable to generate a guide beam from a light in a visible wavelength range, the guide beam being aimable so that the region detectable by the image detector is identified by an indicia having a pattern and projected on the region by the guide beam.

2. The apparatus of claim 1 wherein the excitation light source is operable to generate the light in a non-visible wavelength range between 700 nm and 800 nm.

3. The apparatus of claim 1 further comprising:
    a tripping device operable to actuate recording of a fluorescence image;
    wherein the guide beam is switched off by the actuation of the tripping device.

4. The apparatus of claim 3 wherein the tripping device comprises a button.

5. The apparatus of claim 1 wherein the guide beam projector comprises at least one laser diode.

6. The apparatus of claim 1 wherein the guide beam projector is operable to generate the guide beam so as to project a point-type indicia.

7. The apparatus of claim 1 wherein the guide beam projector is operable to generate the guide beam so as to project a crosshair-like indicia.

8. The apparatus of claim 3 wherein the guide beam projector comprises at least one laser diode.

9. The apparatus of claim 8 wherein the guide beam projector is operable to generate the guide beam so as to project a point-type indicia on the region.

10. The apparatus of claim 8 wherein the guide beam projector is operable to generate the guide beam so as to project a crosshair-like indicia on the region.

11. The apparatus of claim 1, wherein the excitation light source provides a uniform illumination of the region.

* * * * *